United States Patent [19]

Hanin et al.

[11] Patent Number: 4,683,343
[45] Date of Patent: Jul. 28, 1987

[54] ETHER-CONTAINING MIXTURES IN FLEXIBLE PVC

[75] Inventors: Jean A. Hanin, Rixensart; Pierre E. Verrier, Brussels, both of Belgium

[73] Assignee: Exxon Research & Engineering Co., Florham Park, N.J.

[21] Appl. No.: 938,408

[22] Filed: Dec. 5, 1986

Related U.S. Application Data

[62] Division of Ser. No. 803,085, Nov. 27, 1985, Pat. No. 4,656,215.

[30] Foreign Application Priority Data

Nov. 30, 1984 [GB] United Kingdom ................. 8430224

[51] Int. Cl.⁴ ............................................... C07C 43/30
[52] U.S. Cl. .................................... 568/594; 568/671
[58] Field of Search ............... 568/579, 590, 591, 594, 568/671

[56] References Cited

U.S. PATENT DOCUMENTS 2,671,119  3/1954  Mertzweiller ............... 260/604 HF
4,339,389  7/1982  Rogier ..................................... 528/87

FOREIGN PATENT DOCUMENTS 0185477  6/1986  European Pat. Off. ............ 569/594
753560  7/1956  United Kingdom ................ 568/591

OTHER PUBLICATIONS

Russian abstract, 89:52926p by Prokopenko et al, from 80-Organic Anal. Chem., vol. 89, 1978, p. 617.
Jour. of Org. Chem., vol. 26 (1961) pp. 1026–1028–"Hydrogenolysis of Ketals", Howard et al.

Primary Examiner—Joseph L. Schofer
Assistant Examiner—N. Sarofim
Attorney, Agent, or Firm—J. J. Mahon

[57] ABSTRACT

Heavy organic by-products obtained by hydroformylating olefins and hydrogenating the crude product to obtain higher alcohols, and their steam cracked derivatives, have been found useful as viscosity modifiers and low temperature property improvers in flexible PVC compositions.

7 Claims, No Drawings

ETHER-CONTAINING MIXTURES IN FLEXIBLE PVC

This is a division, of application Ser. No. 803,085, filed Nov. 27, 1985, now U.S. Pat. No. 4,656,215.

This invention relates to certain ether-containing mixtures derivable from the crude products of hydroformylation processes and to the use of such mixtures as components of flexible polyvinyl chloride (PVC) compositions.

The hydroformylation process, in general terms, is a process involving the preparation of oxygenated organic compounds by the reaction of carbon monoxide and hydrogen (synthesis gas) with carbon compounds containing olefinic unsaturation. The reaction is performed under hydroformylation conditions in the presence of a carbonylation catalyst or catalyst precursor such as dicobaltoctacarbonyl, and results in the formation of a compound e.g. an aldehyde which has one more carbon atom in its molecular structure than the feedstock. Subsequent hydrogenation of the primary product leads to higher alcohols which may be used for example for conversion into plasticizers.

Typically in higher alcohol production the feedstock for a hydroformylation process is a commercial $C_6$–$C_{12}$ olefin fraction and the desired end product is the respective $C_7$–$C_{13}$ saturated alcohol or derived mixed alcohol product, produced by hydrogenation of the aldehyde oxonation product. By virtue of the nature of the feedstock commonly available to industry, and indeed of the catalyst and reaction parameters employed, the oxonation reaction inevitably yields a range of products due to the numerous secondary reactions which take place. The main commercial products of the hydroformylation reaction are aldehydes and alcohols, with side reactions in the oxonation, demetalling and hydrogenation sections of the process system usually producing some 5 to 20 wt. % of high boiling materials. Such high boiling materials, which represent a serious yield loss to the alcohol producer, are formed in large part by condensation, esterification and dehydration reactions.

In a conventional higher oxo alcohol process, the feedstock as described above is fed together with synthesis gas into an oxonation unit where catalytic hydroformylation takes place using e.g. hydrocobaltoctacarbonyl as the active catalyst species. The oxonation unit product passes to a unit for removing catalyst, and then to a hydrogenation unit where it is hydrogenated to form the desired higher alcohol. The product mixture at this stage, comprising the higher alcohol, the high boiling materials mentioned above and a low boiling fraction is then passed to a distillation unit where low boiling materials, high boiling materials and desired alcohol product are physically separated.

The low boiling material passing off overhead is a low value product, typically containing unreacted olefin feed and paraffins. The high boiling material usually contains dimers such as ethers and ether-alcohols (e.g. $C_{20}$ compounds in $C_{10}$ alcohol production) and trimers such as acetals (e.g. $C_{30}$ compounds in $C_{10}$ alcohol production) and heavier; although substantially alcohol free (apart from the heavy ether-alcohols), it may contain a minor amount of alcohol which has not been removed in the distillation stage where the higher alcohol major target product of the hydroformylation process is separated. Hitherto such high boiling materials or bottoms products have been conventionally purged from the system at low value. It is desirable, therefore, to develop a more profitable use of such materials, and after considerable assessment of the characteristics thereof a surprising new application has been proved.

Some uses have already been proposed, but principally these are directed to uses which involve further treatment of the high boiling materials in order to improve the economics of the oxo process. An example is the teaching of U.S. Pat. No. 4,048,233 (Ruhrchemie AG), according to which high boiling material (termed "thick oil" residue in that document) is converted to synthesis gas ($H_2$/CO mixture) by catalytic splitting at high temperatures using defined proportions of water vapour and carbon dioxide and a catalyst containing from 2 to 25 wt. % nickel, optionally on a carrier such as alumina. The splitting takes place at temperatures of from 600° to 900° C. and pressures up to 30 atmospheres, and the synthesis gas product is recycled to the oxonation unit. Indeed the document teaches that after initial start up the synthesis gas product may constitute the sole supply of said gas to the system.

According to one of its aspects, the present invention provides for the use of a hydroformylation-coproduct mixture as a viscosity regulator and/or low temperature performance improver for flexible polyvinyl chloride (PVC) compositions; such a mixture comprises ether, ether-alcohol and acetal components and is the bottoms product obtained by hydrogenation and subsequent distillation of the crude product derived from the catalytic hydroformylation of a $C_6$–$C_{12}$ olefinic feedstock with synthesis gas.

The hydroformylation process in which the crude product is formed may be considered as entirely conventional and in accordance with the general hydroformylation process disclosures made hereinbefore. Thus the catalyst may be for example cobalt based and the operating temperatures, pressures and other conditions such as synthesis gas composition may be controlled in accordance with the usual expertise of the person skilled in the art to maximise yield of the desired higher alcohol product. For example the hydroformylation reaction may be carried out at a pressure of 150–300 atm, and a temperature of from 125°–175° C. The catalyst may be used in desired active form, for example in a concentration of from 0.05–3 wt. % as metal based on the olefinic feed. Typically the synthesis gas used might have a $H_2$:CO volume ratio in the range 0.9:1–1.5:1.

The mixtures which have been found useful for the purpose defined hereinbefore are preferably those derived from olefinic feedstocks having carbon numbers of 8–9. Preferably such mixtures have a specific gravity of from 0.81–0.87, more preferably 0.83–0.85. It is preferred too that the mixture has distillation characteristics at atmospheric pressure of initial boiling point (IBP) from 240°–310° C., more preferably 260°–300° C. and final boiling point (FBP) from 310°–380° C., more preferably 330°–350° C. Being based on $C_6$–$C_{12}$ feedstock and containing up to trimeric components (or even heavier) by virtue of the nature of the reactions and side reactions occuring under the conditions in the hydroformylation reactor, the mixture used in accordance with the invention will comprise compounds having carbon numbers in the range 7–39.

It is also preferred that the mixtures employed for the specified use are characterised by a flash point of from 140°–170° C. and/or an acidity (mg KOH/g) of from 0.1–3.0, more preferably below 1.0 and/or a hydroxyl number (mg KOH/g) of from 13–160, more preferably below 115 and/or a carbonyl number (mg KOH/g) of from 3-30 and/or a pour point of less than −30° C.

In general coproduct mixtures which have been found to be particularly useful for the specified purpose have from 15-25 wt % ether component, from 45-65 wt % ether-alcohol component from 5-25 wt % acetal component and from 2-10 wt. % of ester component. Depending on the distillation conditions applied following the hydrogenation stage of the hydroformylation process, the bottoms product may contain a minor amount, for example up to 5 wt %, of light alcohol components. However it is preferred that such alcohols be substantially completely removed in order to increase the carbon number range lower limit for alcohols in the mixture to $C_{14}$; the presence of lower molecular weight alcohols in flexible PVC compositions may lead to an odour and/or exudation problem. Preferably the mixtures used comprise a major proportion of compounds with carbon numbers in the range 18-24, and they may also contain a small amount e.g. up to 2 wt. % of extremely heavy compounds.

It has been found that not only is the bottoms product defined and described hereinbefore effective for the specified use in flexible PVC compositions, but so is the derivative of such bottoms product which is obtained by a further steam cracking treatment thereof. Our copending UK patent application No. 84 3022 ref PM 81 ECE 004 and entitled "Hydroformylation of Olefins" describes and claims a process primarily concerned with the production of higher alcohols from an olefinic feedstock. Such process comprises hydroformylating the feedstock with synthesis gas in the presence of a hydroformylation catalyst to form a product mixture containing higher aldehyde, alcohol, unreacted feed and secondary products; removing catalyst therefrom; hydrogenating the substantially catalyst free mixture to convert the higher aldehyde to higher alcohol; distilling the higher alcohol-containing product mixture to separate (i) a lower boiling Light Oxo Fraction (LOF) and (ii) the desired higher alcohol from (iii) a higher boiling Heavy Oxo Fraction (HOF); subjecting the HOF to catalytic steam cracking at a temperature of from 260° to 380° C. using as catalyst an active metal oxide or pseudo-metal oxide, to form HOF residue and a cracked HOF mixture comprising a major proportion of higher alcohol and higher aldehyde, and a minor proportion of olefin and saturated hydrocarbon; and recycling the cracked HOF mixture to the hydroformylation or hydrogenation stage of the process.

In the case where the olefinic feedstock is $C_6$-$C_{12}$, preferably $C_8$-$C_9$, the HOF corresponds to the bottoms product defined hereinbefore, and the catalytic steam cracking step applied thereto results in the formation of an ether-rich derivative termed in our above mentioned copending patent application the HOF residue. This residue has substantially the same type of components as the described bottoms product mixture, but in different proportions and with generally heavier compounds present. Moreover its preferred characteristics of carbon number range, specific gravity, distillation characteristics, flash point, acidity, hydroxyl number, carbonyl number and pour point correspond with those expressed hereinbefore in relation to the bottoms product. A further aspect of the present invention therefore provides an ether-rich hydroformylation-coproduct mixture comprising ether, ether-alcohol and acetal components which is obtained by hydrogenation and subsequent distillation of the crude product derived from the catalytic oxonation of a $C_6$-$C_{12}$ olefinic feedstock with synthesis gas to yield a bottoms product, followed by catalytic steam cracking of such bottoms product at 260°-380° C. using as catalyst an active metal oxide or pseudo metal oxide.

Yet another aspect provides for the use of such an ether-rich hydroformylation-coproduct mixture as a viscosity-regulator and/or low temperature performance improver for flexible polyvinyl chloride (PVC) compositions. In a preferred form the ether-rich derivative comprises from 45-75 wt % ether component, from 20-35 wt % ether-alcohol component and from 1-6 wt % acetal component. Depending on the nature of the further process steps employed to separate the mixture from the other materials formed or present during the cracking stage (water removal, olefin/saturated hydrocarbon removal, aldehyde/ alcohol removal) the mixture may include an alcohol/aldehyde component, for example up to 10 wt %. However as with the bottoms product, this is preferably removed before use in PVC compositions since alcohol/aldehyde components may introduce odour and exudation problems for the proposed use. The derived ether-rich mixtures may, in addition to the components specified above, also contain an ester component for example up to 7 wt. % resulting from the various side reactions which occur in the process by which the mixtures are produced, and for example up to 1 wt. % of extremely heavy compounds.

The ether rich coproduct mixture is generally heavier than the bottoms product, by virtue of the hydrolysis stage and subsequent removal of the alcohol/aldehyde components produced, which are at the lighter end of the carbon number range. Thus the ether-rich material is principally dimers, trimers and even heavier derivatives based on the carbon number of the higher alcohol which is the initial target product of the hydroformylation reaction from which the coproduct mixture is obtained.

This is in comparison with the bottoms product discussed hereinbefore, where principally it is only the lighter alcohols which are preferably removed, but other "monomeric" compounds remain in the mixture.

The catalysts which may be employed to promote hydrolysis of the components of the bottoms product, which generally contains alcohol (assuming not all have been removed in the preceding separation stage), ethers, esters, ether-alcohols and acetals, is selected such that the hydrolysis reaction takes place at the rather severe conditions defined to yield a product mixture which in addition to the ether-rich mixture is relatively enriched in higher alcohols and aldehydes. The catalysed reactions performed under the specified conditions may be for example acetal hydrolysis, ester hydrolysis, or ether hydrolysis.

It has been found that the desired reactions take place in the presence of metal or pseudo-metal oxides in the active state, such as silica, alumina or titanium dioxide, or mixed silica/alumina. It is particularly preferred to employ alumina as the hydrolysis catalyst.

Such catalysts, under the temperature specified, at least partially convert the bottoms product (HOF) to alcohols and aldehydes, and of course to the ether-rich mixture.

The temperature at which the HOF steam cracking step is performed is most preferably in the relatively high range of 290° to 360° C., and preferably at pressures of from 100 to 1000 kPa (1-10 bar), more preferably 1-3 atm abs. It is preferred that the hydrolysis of the HOF is performed with the weight ratio of steam and HOF in the range 0.1:1 to 2:1, more preferably 0.2:1 to 1.2:1. For economic reasons the optimum range has been found to be from 0.15:1 to 0.5:1.

Following steam cracking of the HOF the ether-rich mixture or HOF residue, which is typically oxygenated dimers and trimers ($C_{20}$–$C_{30}+$ materials for a $C_{10}$ alcohol), is separated in a subsequent stage (preferably by a method including steam or flash distillation); however the ether-rich mixture may be automatically separated during the steam cracking step by virtue of the particular cracking technique employed.

The invention defined herein relates to the use of the specified mixtures as a component of flexible PVC compositions. Such compositions, in order to have a degree of flexibility, must contain a plasticizer, and it will be appreciated that the scope of the invention extends not only to the addition of the hydroformylation-coproduct mixtures to the already plasticized PVC, but also to the simultaneous mixing of the mixtures and plasticizer into the PVC, and the admixing of the plasticizer after the oxo-coproduct mixture has been incorporated in the PVC. A further aspect of the invention therefore provides a flexible PVC composition which comprises PVC, a plasticizer therefor, and hydroformylation-coproduct mixture (bottoms product or ether-rich) as hereinbefore defined. Such compositions may be in the form of a plastisol, or for example in the form of heat-fluxed compounds such as calendered or moulded or extruded articles, e.g. extruded cable covering.

It will be appreciated that the plasticizer used should be compatible with the hydroformylation-coproduct mixture, and that the plasticizer and mixture may be added to the PVC as a pre-prepared formulation. It is particularly preferred that the plasticizer should be a phthalate, more preferably one produced by esterification of a higher alcohol produced by a hydroformylation process using olefinic feedstock of carbon numbers corresponding to that employed in the production of the hydroformylation-coproduct mixture itself. Preferred plasticizers which are used in conjunction with the hydroformylation-coproduct mixtures are phthalates of medium range molecular weight such as diisooctylphthalate (DOP), diisononylphthalate (DINP) and diisodecylphthalate (DIDP).

The mixtures, which are believed to function as plasticizers, are preferably used in amounts corresponding to up to 30 wt % of the total plasticizer (conventional plasticizer plus hydroformylation-coproduct mixture) content of the flexible PVC compositions, more preferably 5-30 wt %, and especially 10-20 wt %. Conventionally, flexible PVC compositions contain for example from 50-75 parts by weight of plasticizer per 100 parts by weight PVC, together with, optionally, amounts of filler and other conventional additives depending on the intended end use of the PVC compositions.

It is preferred that the mixtures as specified herein for the stated uses, formulations and compositions are subjected to treatment stages after or during production in order to reduce their odour and/or colour and/or acidity. Conventional finishing techniques may be used for this purpose, and the resulting mixtures, being substantially water white, odourless and of low acidity are of particular value in flexible PVC. The mixtures have been found to be particularly useful when employed with conventional PVC plasticizers to give a desired viscosity reduction of the blends (when in paste form) and/or a useful improvement in low temperature performance e.g. flexibility when in moulded, sheet or extruded form.

The invention is illustrated by the following examples, of which Examples 1 and 3 demonstrate a method of producing a bottoms product form of the oxo-coproduct mixture; Examples 2 and 4 demonstrate the further conversion of such mixtures to their ether-rich forms; and the remaining Examples demonstrate the new uses of the mixtures.

EXAMPLE 1

A hydroformylation process for producing higher alcohol was performed using a feed comprising (i) syn gas containing hydrogen and carbon monoxide in a molar ratio of 1.16:1 and (ii) a commercially available stream of branched nonenes including also about 2 wt % octenes and about 8 wt % decenes. The olefin feed was delivered at a rate of 1.5 l/hr (1115 g/hr), and the syn gas at a rate of 640 standard l/hr, into three 1.0 liter capacity oxonation reactors arranged in series, and the reaction was carried out at a pressure of 300 atm and a temperature of 175° C., using a cobalt catalyst at 0.3 wt % based on the feed. The resultant crude oxo product containing higher aldehyde was decobalted to less than 10 ppm cobalt in conventional manner by neutralizing the cobalt hydrocarbonyl with sodium hydroxide and washing with water, and thereafter was fed to a conventional hydrogenation train where, using Cu/Cr and Ni catalysts, a hydrogen pressure of 50 bar and a temperature of 120°–170° C. a product mixture containing the desired higher alcohol was formed.

This product mixture was then distilled under vacuum to produce three fractions, a light oxo fraction (LOF), a higher alcohol fraction (HA) and a bottoms product or heavy oxo fraction (HOF) as shown in Table 1.

TABLE 1

| Fraction | Amount | Alcohol content | Boiling Range |
| --- | --- | --- | --- |
| LOF | 150 g/hr | ≦0.5 wt % | 125–187° C. |
| HA | 1010 g/hr |  | 187–217° C. |
| HOF | 223 g/hr | ≦3 wt % | >217° C. |

The higher alcohol yield (chiefly $C_{10}$, with minor amounts of $C_9$ and $C_{11}$) was 90.58 g per 100 g of feed olefin.

By analysis the HOF, that is the bottoms product or oxo-coproduct mixture, was shown to comprise approximately:

| 2 wt % | $C_9$–$C_{11}$ alcohols |
| --- | --- |
| 85 wt % | $C_{18}$–$C_{22}$ ethers, ether-alcohols and esters |
| 12 wt % | $C_{27}$–$C_{33}$ acetals |
| 1 wt % | Heavies |

EXAMPLE 2

The bottoms product mixture (HOF) produced in Example 1 was introduced in upflow manner and in admixture with half its weight of steam into a steam cracking reactor. The reactor was packed with an active alumina catalyst ALCOA H151 and operated at 318° C., and a pressure of 1.2 atm. The flow of HOF/steam through the reactor was such as to correspond to a space velocity of 0.5 v/v/hr expressed as volume of HOF per volume of catalyst per hour. After cracking, the cracked product was subjected to flashing at 200° C., to produce an overhead stream comprising a so-called cracked HOF mixture and water (steam), and a bottoms stream of an ether-rich hydroformylation-coproduct mixture (also termed HOF residue). The HOF residue (54 g/hr) comprised a major proportion of oxygenated compounds of carbon number $C_{18}$–$C_{30}$ (predominantly $C_{18}$–$C_{22}$) with some even heavier products, and a minor proportion (6.2 wt %) of alcohol/aldehyde/olefin components. The cracked HOF mixture (169 g/hr) obtained after condensation of the overheads and separation of water comprised a small proportion of HOF residue, a smaller proportion of an olefin fraction, generally $C_8$–$C_{11}$ olefins with predominantly $C_{10}$ olefin and a very low level of saturated hydrocarbon, and a major proportion of an alcohol/aldehyde mixed fraction with carbon numbers $C_9$–$C_{11}$, predominantly $C_{10}$.

EXAMPLE 3

A hydroformylation process was performed in the same apparatus as Example 1 under conditions of 165° C., 300 atm and using cobalt catalyst at 0.15 wt % based on the feed. However, the feed in this case was 1.5 l/hr (1095 g/hr) of a commercial branched octene feed containing in addition to $C_8$ olefin, about 1% of $C_7$ olefins and about 10% of $C_9$ olefins. The syn gas was employed at a rate of 750 standard liters/hr, and contained hydrogen and carbon monoxide in a ratio of 1.18:1.

Demetalling and hydrogenation of the crude product was performed as in Example 1, with the hydrogenated product being separated by distillation into the three fractions as shown in Table 2. The hydroformylation-coproduct mixture (HOF) was the fraction boiling at 206° C. and above.

TABLE 2

| Fraction | Amount | Alcohol content | Boiling Ranges |
|---|---|---|---|
| LOF | 150 g/hr | >0.5 wt % | 113–184° C. |
| HA | 1013 g/hr |  | 184–206° C. |
| HOF | 219 g/hr | ≦3 wt % | >206° C. |

This yield of higher alcohol corresponds to an amount of 92.5 g per 100 g of feed olefin.

By analysis the HOF was shown to have the composition:

| | | |
|---|---|---|
| 1 | wt % | $C_8$–$C_{10}$ alcohols |
| 87 | wt % | $C_{16}$–$C_{20}$ ethers, esters and ether-alcohols |
| 11 | wt % | $C_{24}$–$C_{30}$ acetals |
| 1 | % | Heavies |

EXAMPLE 4

The bottoms product hydroformylation-coproduct mixture produced in Example 3 was subjected to catalytic steam cracking in a reactor packed with ALCOA H 151, at 310° C., a pressure of 1.1 atm and a space velocity of HOF equal to 0.47 v/v/hr. The amount of steam used was 25% of the weight of HOF. Two cracked product streams were obtained following flash at 196° C. and removal of water. The ether-rich mixture (HOF residue) stream (46 g/hr) was the flash liquid phase and was found to comprise $C_{10}$–$C_{27}$ oxygenated compounds, predominantly $C_{16}$–$C_{20}$ materials, with 7 wt % other minor components including some aldehyde, alcohol and olefin. The other stream (173 g/hr), being the flash vapour phase, comprised an olefin fraction (10 wt %) which was a mixture of $C_7$–$C_{10}$ olefins, predominantly $C_9$'s together with small amounts of saturated hydrocarbons, and an alcohol/aldehyde fraction (69.2 wt %) containing a $C_8$–$C_{10}$ carbon number range, with a major amount of $C_9$ alcohols/aldehydes.

EXAMPLE 5

Plastisols, that is pastes comprising PVC-Solvic 367 NC (100 parts by weight) and a plasticizer formulation (60 parts by weight) were produced using a range of formulations by a simple mixing technique. Plastisols are conventionally used for forming at room temperature into required shapes (e.g. of gloves, wall coverings, tarpaulins) followed by heating to yield generally flexible artefacts. It is important, therefore, that plastisols should have viscosity characteristics (initial and after ageing) which are suitable for this use. The plastisols produced were subjected to medium-high shear rate viscosity measurement using a Haake viscometer. This instrument comprises coaxial cylinders, the inner one of which is mobile. The material under measurement is contained as a film between the two cylinders. Measurements were made at a rate of 644 sec$^{-1}$ and at room temperature (23° C.), initially immediately after production of the plastisol and then after ageing for 72 hours. The results are shown in Table 3, from which it may be seen that the inclusion of both bottoms product hydroformylation-coproduct mixture and its ether-rich derivative in flexible PVC compositions has a viscosity depressing effect which is maintained even after ageing. The viscosity depressing effect was seen at both high and low shear rates in the viscosity measurement technique which was employed.

TABLE 3

| | Example Number | | | |
|---|---|---|---|---|
| | 5A | 5B | 5C | 5D |
| Plasticizer formulation (60 phr) | | | | |
| Phthalate | DOP | DINP | DINP | DINP |
| Coproduct (%) | — | — | 10(a) | 10(b) |
| Initial viscosity (poises) | 27 | 25 | 22 | 18 |
| 72 hour viscosity (poises) | 38 | 29 | 23 | 20 |

(a) = Bottoms product hydroformylation-coproduct mixture produced in Example 1
(b) = Ether-rich hydroformylation-coproduct mixture produced in Example 2

EXAMPLE 6

A PVC cable composition was prepared by admixing PVC-Solvic 271 GB (100 parts), calcium carbonate filler (80 parts), plasticizer formulation (50 parts), tribasic lead sulfate heat stabilizer (4 parts) and dibasic lead stearate lubricant (1 part). Various plasticizer formulations were employed, including straight DOP, straight DIDP, a formulation with added mixture according to the invention, and a conventional formulation of 70% DOP with 30% Cereclor S 52, a known chloroparaffin secondary plasticizer. The cable composition was moulded into pads which were then subjected to various tests including volatility (7 days at 100° C.); heat stability (specification VDE 0271 at 200° C.); pad volume resistivity at 70° C.; and retained elongation after ageing for 7 days at 100° C. Results are shown in Table 4, from which it may be seen that the use of a mixture in accordance with the invention results in compositions having characteristics which are highly acceptable to the cable industry.

TABLE 4

| | Example Number | | | |
|---|---|---|---|---|
| | 6A | 6B | 6C | 6D |
| Plasticizer formulation | | | | |
| Phthalate | DOP | DIDP | 70 DOP | DIDP |
| Coproduct (%) | — | — | — | 10(c) |
| Chlorinated paraffin (Cereclor S 52) | — | — | 30 | — |
| Volatility after 7 days at 100° C. (mg/cm$^2$) | 4.5 | 0.7 | 4.1 | 1.8 |
| Retained elongation after 7 days at 100° C. (%) | 0 | 91 | 0 | 98 |
| Heat stability at 200° C. 73 (minutes) | 96 | 30 | 82 | |
| Pad volume resistivity at 70° C. (10$^{11}$ ohm cm) | 3.1 | 2.4 | 6 | 1.7 |

(c) = the hydroformylation-coproduct mixture produced in Example 1

EXAMPLE 7

A typical PVC shoe compound was produced by melting a mixture of PVC-Solvic 264 GA (100 parts) and plasticizer formulation (75–85 phr) and thereafter forming the melt into a moulded sheet form. Various plasticizer formulations were employed, and the resultant compound was in each case subjected to tests including volatility (7 days at 100° C.); retained elongation after 7 days at 100° C.; and flexibility measurements (Clash and Berg test, Falling Hammer test). Results are shown in Table 5, from which it may be seen that the use of hydroformylation coproduct mixtures in accordance with the invention leads to a highly desirable improvement in the low temperature flexibility characteristics of the PVC compounds.

In this specification, where reference is made to a particular mixture having a particular carbon number range or containing a major proportion of compounds having such particular carbon number range, it is meant that more than 50% by weight of the mixture comprises compounds in that carbon number range. In all such cases it is preferred that such proportion is greater than 80% by weight, and more preferably greater than 90% by weight.

TABLE 5

| | Example Number | | | | | | | |
|---|---|---|---|---|---|---|---|---|
| | 7A | 7B | 7C | 7D | 7E | 7F | 7G | 7H |
| Plasticizer (phr) | 75 | 80 | 83.5 | 83 | 84 | 79 | 75 | 73.5 |
| Formulation | | | | | | | | |
| Phthalate | DOP | DINP | 70 DOP | DINP | DINP | DINP | C$_{6-10}$ | C$_{7-11}$ |
| Coproduct (wt % on formulation) | — | — | — | 10(d) | 15(e) | — | — | — |
| Other plasticizer (wt % on formulation) | — | — | 30 CERECLOR S 52 | — | — | 20 DINA | — | — |
| Clash-Berg flex T$_f$ (°C.) | −43 | −42 | −42 | −49 | −53 | −46 | −53 | −49 |
| Falling Hammer flex (°C.) | −41 | −40 | −38 | −45 | −50 | −47 | −52 | −50 |
| Volatility after 7 days at 100° C. (mg/cm$^2$) | 7.2 | 2.2 | 5.4 | 4.0 | 4.8 | 4.2 | 3.1 | 2.6 |
| Retained elongation after 7 days at 100° C. (%) | 71 | 98 | 87 | 88 | 90 | 53 | 94 | 89 |

(d) = hydroformylation-coproduct of Example 1
(e) = hydroformylation-coproduct of Example 2
C$_{6-10}$ = linear phthalate plasticizer of carbon number 6-10
C$_{7-11}$ = linear phthalate plasticizer of carbon number 7-11

We claim:

1. An ether rich hydroformylation-coproduct mixture comprising ether, ether-alcohol and acetal components which is obtained by hydrogenation and subsequent distillation of the crude product derived from the catalytic hydroformylation of a C$_6$-C$_{12}$ olefinic feedstock with synthesis gas to yield a bottoms product, followed by catalytic steam cracking of such bottoms product at 260°–380° C. using as catalyst an active metal oxide or pseudo metal oxide.

2. A mixture according to claim 1 wherein said steam cracking catalyst comprises alumina.

3. A mixture according to claim 1 having physical and chemical properties selected from a specific gravity of from 0.81–0.87, distillation characteristics at atmospheric pressure of initial boiling point from 240°–310° C. and final boiling point from 310°–380° C., and a major proportion of compounds with carbon numbers in the range 7–39.

4. A mixture according to claim 1 having physical and chemical properties selected from a flash point of from 140°–170° C., an acidity (mg KOH/g) of from 0.1–3.0, an hydroxyl number (mg KOH/g) of from 13–50, a carbonyl number (mg KOH/g) of from 10–130 and a pour point below −30° C.

5. A mixture according to claim 1 which comprises from 45–75 wt % ether component, from 20–35 wt % ether-alcohol component, from 1–6 wt % acetal component.

6. A mixture according to claim 1 which contains substantially no alcohol and comprises a major proportion of compounds with carbon numbers in the range 14–39.

7. A mixture according to claim 6 which comprises a major proportion of compounds with carbon numbers in the range 18–24.

* * * * *